United States Patent [19]

Parekh et al.

[11] Patent Number: 5,427,744
[45] Date of Patent: Jun. 27, 1995

[54] SEQUENCING OF OLIGOSACCHARIDES

[75] Inventors: Rajesh B. Parekh, Oxford; Sally B. Prime, Oxon, both of United Kingdom

[73] Assignee: Oxford Glycosystems Ltd., Oxon, United Kingdom

[21] Appl. No.: 140,143

[22] PCT Filed: May 7, 1992

[86] PCT No.: PCT/GB92/00831
§ 371 Date: Nov. 3, 1993
§ 102(e) Date: Nov. 3, 1993

[87] PCT Pub. No.: WO92/19766
PCT Pub. Date: Nov. 12, 1992

[30] Foreign Application Priority Data

May 7, 1991 [GB] United Kingdom ............... 9109842

[51] Int. Cl.⁶ ............................................. G01N 33/50
[52] U.S. Cl. ................................. 422/116; 435/101; 435/291
[58] Field of Search ................. 422/116; 435/4, 18, 435/101, 291

[56] References Cited

U.S. PATENT DOCUMENTS 5,100,778 3/1992 Rademacher et al. ............... 435/18

FOREIGN PATENT DOCUMENTS

0421972A2 10/1990 European Pat. Off. .
WO92/02816 2/1992 WIPO .

OTHER PUBLICATIONS

Joseph K. Welply: "Sequencing methods for carbohydrates and their biological applications"; *TIBTECH;* 7 (1989) Jan.; pp. 5–10.

*Primary Examiner*—Timothy M. McMahon
*Attorney, Agent, or Firm*—Oliff & Berridge

[57] ABSTRACT

The present invention relates to the analysis of unknown oligosaccharides and more particularly the form of analysis in which an unknown oligosaccharide is sequentially brought together with different agents which cause monosaccharides to be cleaved from (or chemically bound to) the oligosaccharide. If cleavage occurs the monosaccharide will subsequentially be detected in the products of the experiment thus confirming that the monosaccharide was attached to the unknown oligosaccharide and providing a means of determining the structure of the unknown oligosaccharide. The invention proposes an analytical technique for determining the best agent to be used in performing such an experiment so that a maximum amount of information is obtained from the experiment.

13 Claims, 5 Drawing Sheets

Legend
Man - Mannose
Gal - Galactose
Fuc - Fucose
Glcnac - N-acetyl glucosamine

SEQUENCING OF OLIGOSACCHARIDES

This is a continuation of PCT/GB92/00831 filed on Apr. 7, 1992 which is now WO 92/19766.

The present invention relates to the analysis of oligosaccharides and more particularly to the form of analysis known as sequencing of oligosaccharides.

Oligosaccharides form a class of chemical compounds which are each made up of a number of monosaccharide units linked together by glycosidic bonds. Important sources of naturally occurring oligosaccharides are glycoproteins in which oligosaccharides are found linked to a peptide chain by either an N-glycosidic bond or by an O-glycosidic bond; these oligosaccharides may vary up to highly branched structures containing many (e.g. over 30) monosaccharide units.

In a sequential analysis of an unknown oligosaccharide structure, a single reaction is performed with a particular reagent on a pure sample of the unknown oligosaccharide and its products analysed. The reagent is chosen such that the product of the reaction will reveal the presence or absence of a particular structural sub-unit or sub-units which may or may not occur in the sample. Based on the results of this analysis, a further reaction may be carried out using a different reagent, either with more of the original pure sample or with the products of the previous reaction. From the analysis of the second reaction further conclusions may be drawn about the structure of the original oligosaccharide sample and the process repeated as often as necessary, until as much information as possible has been extracted about the original oligosaccharide structure with the reagents available or until supplies of the pure sample and derived products have been exhausted. The end point of any analysis of an oligosaccharide structure, whether the analytical technique is sequential or not, is to deduce information concerning the oligosaccharide structure; this information includes, (i) the type of each monosaccharide unit in the oligosaccharide, (ii) the order in which the monosaccharide units are arranged in the oligosaccharide, (iii) the position of linkages between each of the monosaccharide units (e.g. 1-3, 1-4), and hence any branching pattern, (iv) the orientation of the linkage between each of the monosaccharide units (i.e. whether a linkage is an alpha linkage or a beta linkage).

An agent which assists in this process of structural analysis may be regarded as a "sequencing agent". Where a sequencing agent is a chemical or biochemical reagent the sequencing agent may be regarded as a sequencing reagent. Examples of sequencing reagents are enzymes and typical enzymes used in sequencing oligosaccharides are listed in the Enzyme Rules Table set out below.

Enzyme Rules Table
The following is a list of the enzymes commonly used for cleaving monosaccharides from N-linked oligosaccharides and the rules showing which monosaccharides are cleaved by each of these enzymes and from which part of the oligosaccharide structure cleavage can be expected.

| Enzyme | Monosaccharide Cleaved | Rules for Cleavage |
|---|---|---|
| 1) Achatina fulica beta mannosidase | Mannose | 1-beta-4 to any site |
| 2) A.saitoi alpha mannosidase | Mannose | 1-alpha-2 to any site |
| 3) Jack bean alpha mannosidase | Mannose | 1. mannose 1-alpha-2 to any site 2. cleaves the 1-alpha-3,6 mannoses if there is no bisect on the middle mannose |
| 4) Jack bean alpha mannosidase (under arm-specific conditions) | Mannose | Different from 3) in that it will not cleave the mannose 1-alpha-6 case when restricted by a side arm longer than 1 unit out from the middle mannose |
| 5) Bovine testis beta galactosidase | Galactose | 1-beta-3,4 to any non-branched site |
| 6) Jack bean beta galactosidase | Galactose | 1-beta-4 to any non-branched site |
| 7) C.lampas beta xylosidase | Xylose | 1-beta-any to any site |
| 8) S.pneum beta N-acetyl hexosaminidase | N-acetyl hexosamine | 1. 1-beta-3 to any non-branched site 2. 1-beta-2 mannose 1-alpha-3 or 6 to middle mannose provided the first mannose does not have a bond at atom 6, and also in the case of 1-alpha-6 that the middle mannose is not bisected |
| 9) Jack bean beta N-acetyl hexosaminidase | N-acetyl hexosamine | 1-beta-any to any site |
| 10) Bovine epididymis alpha fucosidase | Fucose | 1-alpha-3,4,6 to any site |
| 11) C.lampas alpha fucosidase | Fucose | 1-alpha-2,3,4,6 to any site |
| 12) Coffee bean alpha galactosidase | Galactose | 1-alpha-3,6 to any non-branched site |
| 13) Almond alpha fucosidase | Fucose | 1-alpha-3,4 to any site |

It will be appreciated that a sequencing agent may be chosen such that the products obtained when it is brought into contact with an unknown oligosaccharide will reveal (in later analysis) the presence or absence of a particular structural sub-unit (e.g. a monosaccharide unit) in the oligosaccharide. It will also be appreciated that by sequentially contacting either samples of the original oligosaccharide or products thereof (produced by previously contacting samples of the oligosaccharide with one or more sequencing reagents) with a sequencing reagent, it is possible to deduce that the unknown oligosaccharide contains a certain structure or structures or does not contain a certain structure or structures.

For example, the presence and linkage of a particular monosaccharide at the terminus of an oligosaccharide may be confirmed by the ability of a given sequencing agent, such as an enzyme, to cause cleavage of that linkage; thus, if cleavage occurs when that enzyme is brought together with the oligosaccharide, then detection of that particular monosaccharide (now detached from the oligosaccharide) in the products of the reaction will confirm the presence of that monosaccharide and will define the position and orientation of the linkage of that monosaccharide in the original oligosaccharide structure. Thus, by sequentially using a plurality of different sequencing agents having specific linkage cleaving capabilities, it is possible to deduce increasing amounts of information regarding the structure of the oligosaccharide under analysis.

Where no single sequencing agent can be found that can increase the amount of information about the structure of the unknown oligosaccharide then consideration can be given to possible combinations of two, three or more agents being applied one after the other; at each stage of consideration an agent which does not produce a meaningful result may be discarded, although the fact that it did not react with the oligosaccharide to produce products may allow deductions to be made regarding the structure of the oligosaccharide. Consideration may also be given to using a combination of two or more agents applied simultaneously.

For the purposes of this specification, a sequencing agent or reagent can be an agent or reagent which either cleaves or forms chemical bonds when brought into contact with an unknown oligosaccharide.

The effectiveness of the sequencing method depends critically upon the choice of agent to be used at each stage of each reaction process and the accuracy of the interpretation of the results of each analysis. At present, to a large degree, a good choice of agent requires an experienced operator who has already made some intelligent guesses about the type of structure being dealt with. A poor choice may result in little or no additional information being revealed by a particular experiment, resulting in the process being wasteful of both time and materials. There is also the danger that the prejudices of the operator will mask ambiguities in the interpretation of the results. Thus, the operator may assign a single structure which is consistent with the experimental results, whereas in reality there may be more than one structure consistent with the same set of observations. A further difficulty arises in defining the point at which no further information can be revealed by the use of the agents available.

The sequencing of oligosaccharides may be assisted by a knowledge of the biosynthetic pathways involved in building up the oligosaccharide structures.

Thus, for example, for N-linked oligosaccharides (N-glycans) it is known that there is a characteristic core structure and that monosaccharides may only add on in certain well defined orders and branching patterns. This knowledge may be used to develop the concept of 'basic' or 'core' structures for oligosaccharides from which sets of sub-structures can be generated by performing specific transformations on the 'basic' structures.

BRIEF DESCRIPTION OF THE DRAWINGS

In the accompanying drawings three 'basic' structures are shown respectively in FIGS. 1 to 4. The illustrated 'basic' structures are not all the structural possibilities for N-glycans and are shown by way of example only.

In the case of these structures, the transformation used to generate the sub-structures is successive deletion of terminal monosaccharides. Numerous sub-structures can thus be formed starting with a 'basic' structure and, for example, successively deleting monosaccharides in all possible ways. There are several different patterns of deletion of monosaccharides possible leading to a very large number of sub-structures which can be derived from the 'basic' structures. The number of sub-structures which can be generated by transformation from the three illustrated sub-structures, is, therefore, very large. In carrying out an analysis of an unknown oligosaccharide, an initial analysis will allow a first judgement to be made that the oligosaccharide belongs to a particular set of sub-structures. This leads to the term "candidate structure" which is used herein to refer to a structure which is included in the set of sub-structures as being a possible candidate for having the same structure as the unknown oligosaccharide.

Figure 1:
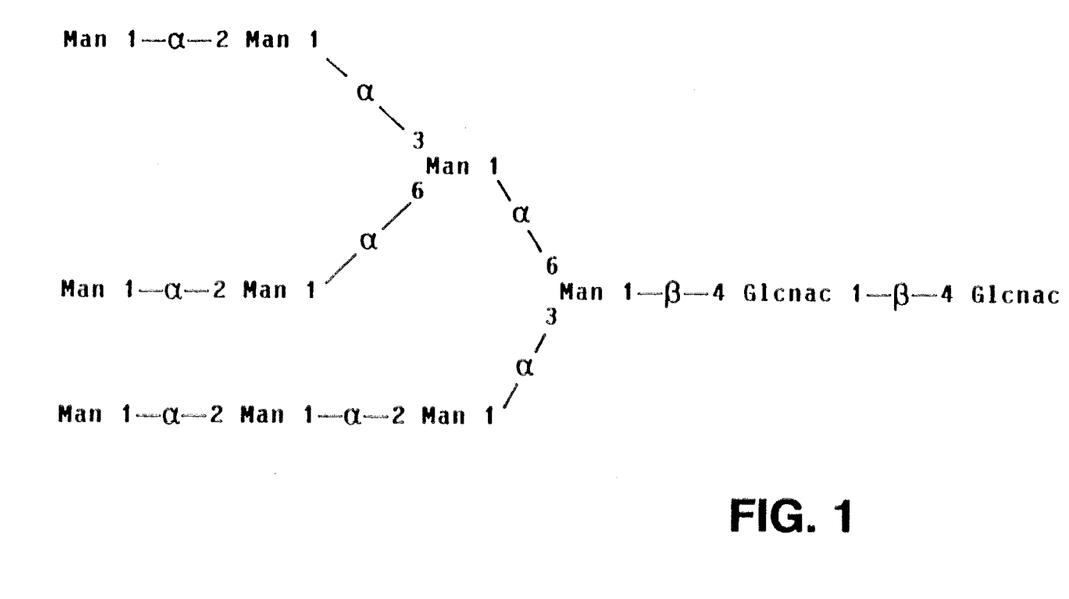
Figure 2:
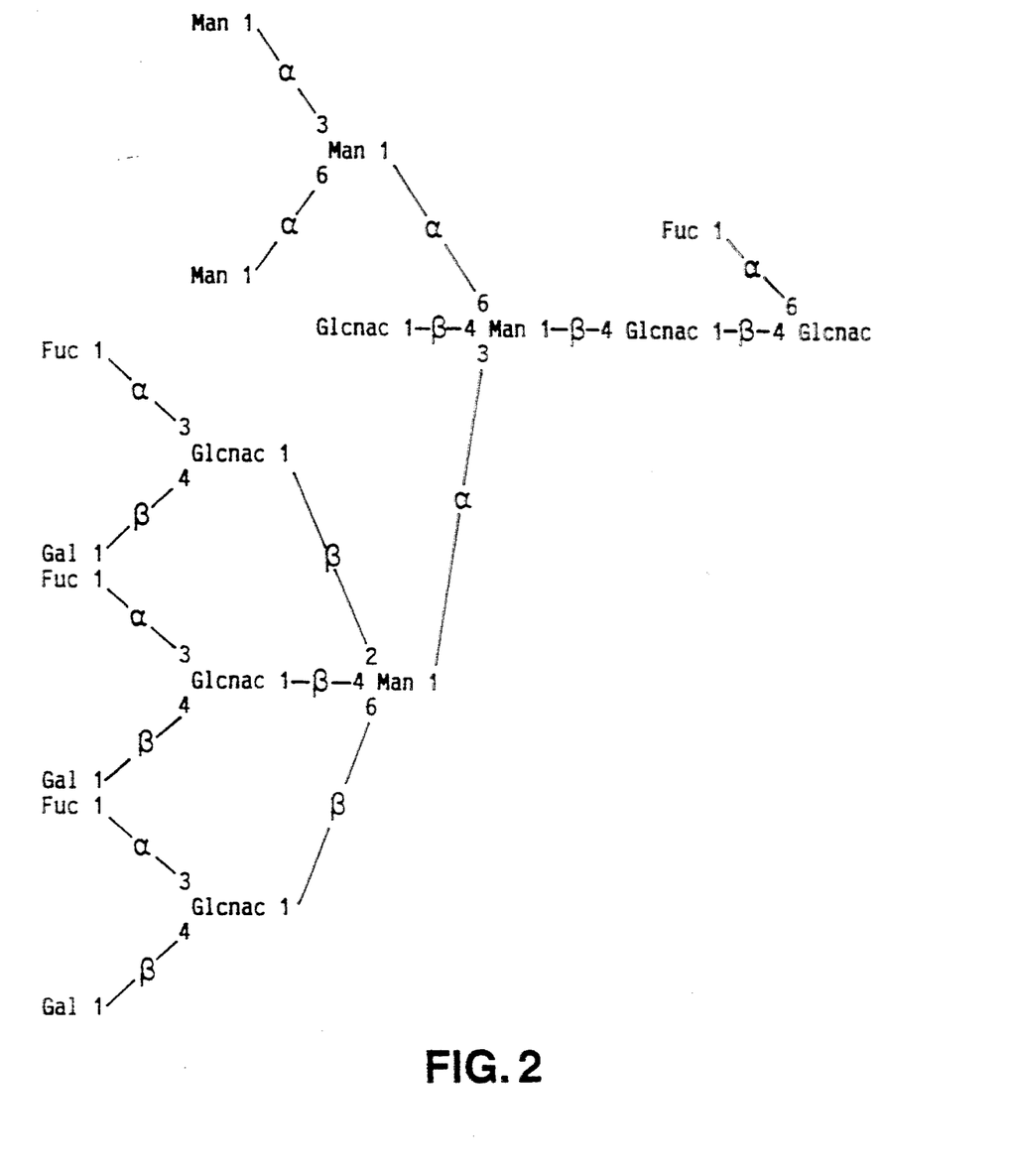
Figure 3:
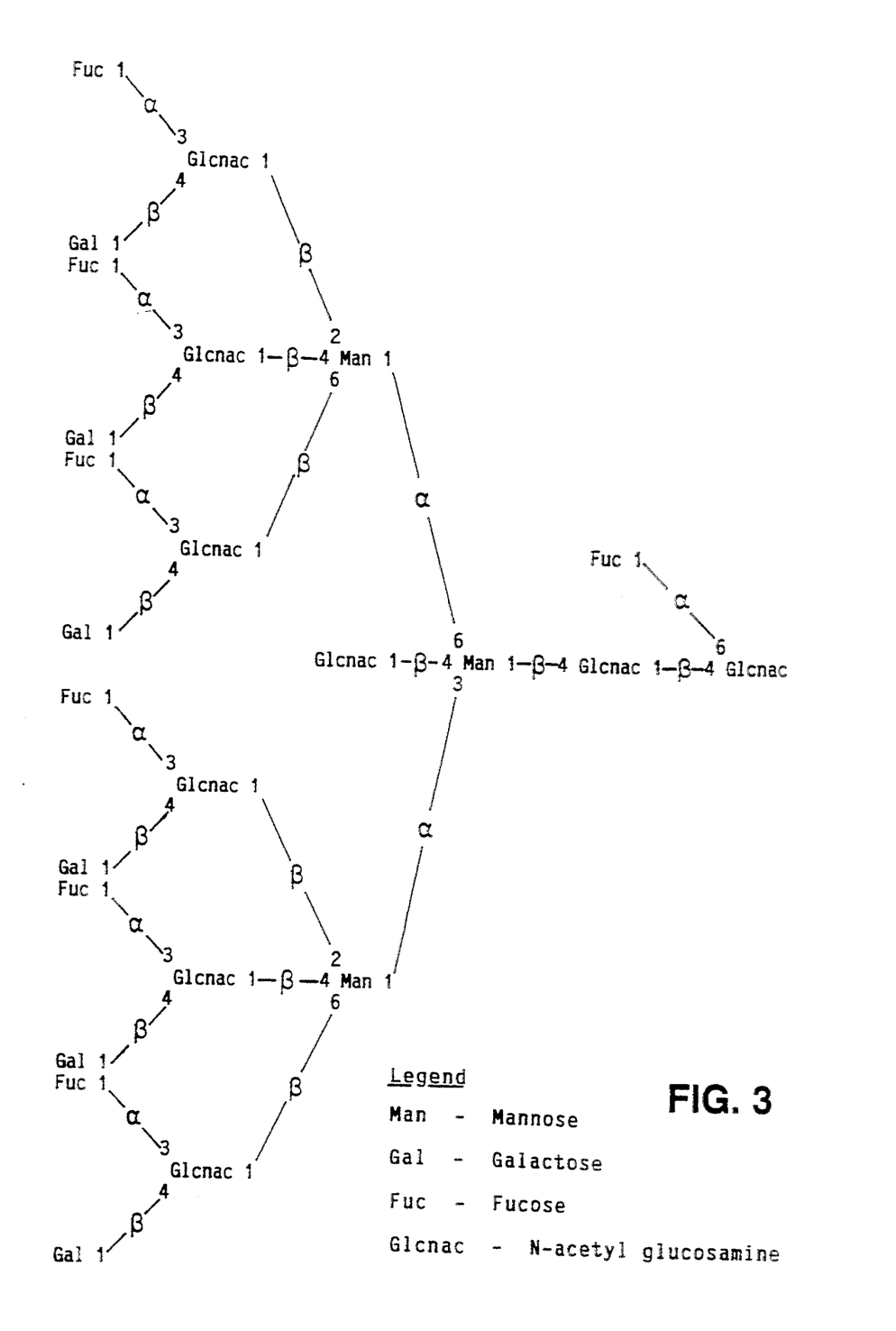

For example, if the oligosaccharide to be sequenced has been purified from a mixture of oligosaccharides released from a glycoprotein by the use of enzyme peptide-N-glycosidase F, then it can be assumed that the oligosaccharide is an N-glycan and that its structure is likely to be one of the sub-structures generated from 'basic' structures similar to the ones illustrated in FIGS. 1 to 3.

However, because such a set of sub-structures can be very large, it is desirable to reduce the size of the initial set of candidate structures as much as possible. One way of approaching this problem is to consider one property of the sample to be sequenced which depends in some way upon its structure. Examples of such properties are:

i) the molar proportion of each monosaccharide (composition analysis)
ii) the retention time of the sample on a chromatographic column, which may be expressed in glucose units These properties can be calculated for each sub-structure, and only those structures whose properties are the same as those of the sample to be sequenced need be retained for further consideration as candidates for the unknown structure.

The presence and linkage (both position and orientation) of a particular monosaccharide at the terminus of an oligosaccharide can be confirmed if it is known that a given enzyme will cause cleavage of that monosaccharide (and nothing else). If cleavage occurs, then detection of that monosaccharide in the products of the reaction confirms the presence of the linkage in the original structure.

For each enzyme used as a sequencing reagent, it can be established which monosaccharides will be cleaved from a particular 'basic' oligosaccharide structure. The rules for such cleavage for a number of enzymes are set out in the Enzymes Rules Table above. By applying rules such as these to each candidate structure it is possible to determine for each candidate structure the monosaccharides which will be cleaved by bringing each enzyme in turn into contact with it.

The present invention provides a way of optimising the use of sequencing agents, interpreting the results unambiguously and determining the point where no further sequencing with the available reagents is possible. According to the present invention there is provided apparatus for sequencing an unknown oligosaccharide, comprising first means for deducing a set of oligosaccharide structures of which the unknown oligosaccharide is assumed to be a member, second means for simulating the effect of applying each one of a series of sequencing agents to each of said set of oligosaccharide structures and third means for determining the sequencing agent likely to give the most structural information if applied to the unknown oligosaccharide.

The invention also provides a method of sequencing an unknown oligosaccharide comprising deducing a set of oligosaccharide structures of which the unknown oligosaccharide is assumed to be a member, simulating the effect of applying each one of a series of sequencing agents to each of said set of oligosaccharide structures and determining the sequencing agent likely to give the most structural information if applied to the unknown oligosaccharide.

Preferably, the invention includes performing an initial analysis whereby to identify at least one basic structure (as herein defined) from which the said set of oligosaccharide structures can be generated.

Preferably also, the invention includes contacting the unknown oligosaccharide with the agent or agents selected in accordance with a set of rules for the use of sequencing agents and comparing the actual experimental result with the calculation.

The method of the present invention postulates an initial set of candidate structures and allows a calculation to be made to determine the most efficient experiment to be performed at any given time. Structures inconsistent with the results of this experiment are then eliminated from the existing set and the next experiment determined based on the structures remaining. The process is repeated until no further elimination is possible with the given sequencing agents.

By performing an exhaustive search among the known products of reaction of all candidate structures with the available sequencing reagents, it is possible to determine the optimum sequencing reagent or series or mixtures of sequencing reagents, such that the largest possible number of candidate structures can be eliminated by performing the reaction with this reagent and determining the products.

In order to determine the most efficient experiment to be carried out, consideration must then be given to the known results of applying each of the available reagents to the remaining candidate structures.

As an example, assuming that the initial composition analysis indicates that the unknown oligosaccharide is a member of a set of candidate structures denoted [A, B, C, D] and that enzymes 1, 2, 3, 4 are the available sequencing reagents. The results of applying these enzymes to these structures can be predicted by applying enzyme rules such as those set out in the Enzyme Rules Table above, to each structure in turn. The rules, for example, might indicate that enzyme 1 will cleave the monosaccharide mannose from each of the candidate structures as follows, Candidate A, enzyme 1 cleaves 1 mannose
Candidate B, enzyme 1 cleaves 1 mannose
Candidate C, enzyme 1 cleaves 0 mannose
Candidate D, enzyme 1 cleaves 2 mannose Assume, for example, that the full results of applying each enzyme to each candidate structure are as follows,

| Candidates | A | B | C | D |
|---|---|---|---|---|
| Enzyme 1 | 1 mannose | 1 mannose | 0 mannose | 2 mannose |
| Enzyme 2 | 1 fucose | 0 fucose | 0 fucose | 0 fucose |
| Enzyme 3 | 2 galactose | 2 galactose | 2 galactose | 2 galactose |
| Enzyme 4 | 1 mannose | 0 mannose | 0 mannose | 2 mannose |

The question to be answered in this example is, which, if any, of the candidate set [A, B, C, D] is the actual structure of the unknown sample. It must be determined which of the available sequencing reagents (in this example enzymes 1 to 4) is the best one to use to help find the answer to that question most efficiently. This is done by considering a Breakdown Result (a) for each enzyme derived from data in the above tables. A Breakdown Result groups the candidate structures into subsets where all the members of that subset give the same result in terms of the number of monosaccharides cleaved when reacted with the enzyme.

Also, for each Breakdown Result (a), a Breakdown Entropy (b) can be calculated to give a numerical measure of the efficiency of each enzyme. The Breakdown Entropy (b) is the sum over all the subsets in a Breakdown Result (a) of the term, $$-N(i) * \log N(i)$$

where $N(i)$ is the length of the ith subset, i.e. the number of candidate structures in the ith subset.

The above table of data can therefore be expressed in terms of Breakdown Results (a) and Breakdown Entropy (b),

| (a) | enzyme 1, subset ([A, B],1), subset ([C],0), subset ([D],2) |
|---|---|
| (b) | entropy 1 = −(2 * log2 + 1 * log1 + 1 * log1) = −0.602 |
| (a) | enzyme 2, subset ([A],1), subset ([B, C, D],0) |
| (b) | entropy 2 = −(1 * log1 + 3 * log3) = −1.431 |
| (a) | enzyme 3, subset ([A, B, C, D],2) |
| (b) | entropy 3 = −(4 * log4) = −2.408 |
| (a) | enzyme 4, subset ([A, D],1), subset ([B, C],2) |
| (b) | entropy 4 = −(2 * log2 + 2 * log2) = −1.204 |

The Breakdown Entropy of an enzyme is a direct measure of the scatter of the structures in the candidate set among different possible experimental outcomes from applying that enzyme. When all experimental outcomes are the same, the Breakdown Entropy has its minimum value (as in the above example for enzyme 3), and it is clear that it is impossible to distinguish between the candidate structures by performing that experiment. Conversely, if all experimental outcomes are distinct, the Breakdown Entropy is identically zero, which is its maximum possible value, and performing that experiment will identify uniquely the structure being sought. In general, the enzyme with the maximum Breakdown Entropy is chosen so as to give the highest statistical chance of rapidly eliminating structures from the set of candidates. In the example above therefore, enzyme 1 would be chosen.

The Breakdown Entropy is the primary index of evaluation in the search for the best sequencing experiment. An enzyme can be eliminated from further consideration in the search under the following criteria, A) if the enzyme would not cleave any monosaccharides from any of the candidate structures, B) if the Breakdown Entropy is less than that of some other enzyme, C) if the enzyme cleaves more monosaccharides than some other enzyme which has an equal Breakdown Entropy, D) if the enzyme is more expensive to use than another enzyme which offers an equal result.

If a first generation search (i.e. a search on the original sample) using all available enzymes, yields no single enzyme with a Breakdown Entropy greater than the minimum, then a second generation search (i.e. a search on the residue from the first generation search) using two enzymes, either together or in sequence is performed, and failing that, third generation, fourth generation, etc., searches are performed, until the point is reached where the candidate structures are deemed indistinguishable because all enzyme mixtures being tested would reduce all candidate structures to a common residue. At this point it is possible to conclude that there is no experiment with the available sequencing reagents which could further reduce the size of the set of candidate structures.

The method can be carried out as a series of logical steps, not all of which need to be performed in every case:

1. Initialisation 1.1 Specify a set of 'basic' structures 1.2 Specify sample composition 1.3 Generate all the sub-structures from the 'basic' structures in 1.1 having the composition given in 1.2. These form the initial set of candidate structures 2. Calculation 2.1 Search for the best reagent 2.1.1 For each reagent calculate a Breakdown Result listing the number of monosaccharides cleaved from each 'basic' structure by that reagent.

2.1.2 Compare the results using criteria A to D above and select the best Breakdown Result, 2.1.2.1 If no Breakdown Result is found which contains two or more subsets of residues which give different results when the reagent is applied, then select the next best Breakdown Result.

2.1.2.2 If no single reagent can be found that can distinguish between the candidate structures, then the search is repeated using all possible series of two, three or more reagents applied one after the other. At each stage, reagents which have no effect on any of the candidate structures are eliminated from the search. If a series of one or more sequencing reagents is found which produces a distribution entropy greater than the minimum, then this series of experiments is chosen to be performed sequentially on the sample.

a. Experiment 3

3.1 Carry out the experiment(s) indicated by 2. above

4. Result

Check the results against predictions, 4.1 Compare the number of monosaccharides cleaved using the recommended reagent with the prediction for each subset in the Breakdown Result for that enzyme.

4.2 If the sample is identified as a member of one of the subsets of structures in the Breakdown Result in that it matches in the number of monosaccharides cleaved with the experimental result, it may be that further information can be obtained. A further set of calculations can be performed by re-defining the set of candidate structures as the subset of structures identified in the Breakdown Result.

4.3 If no subset of the Breakdown Result matches the experimental result then it is likely that either, i) the experiment has failed, or ii) the initial assumptions about the 'basic' structures were invalid.

Overall

It is clear that the amount of calculation to be performed can be considerable. The method is, therefore, best performed using a computer and a program can be written to carry out the calculations and allow the user to make the choices needed to select the experiments. However, the kind of decisions to be made are essentially those which an expert can perform and a computer expert system has been developed to perform the logical operations involved.

To test the accuracy of this computer expert system a known, pure oligosaccharide was analysed using, for reference, the three 'basic' structures shown in FIGS. 1 to 3. The total number of structural variants generated from the three 'basic' structures by cleaving monosaccharides in all known ways from these three oligosaccharides, is about 70,000.

Figure 4:
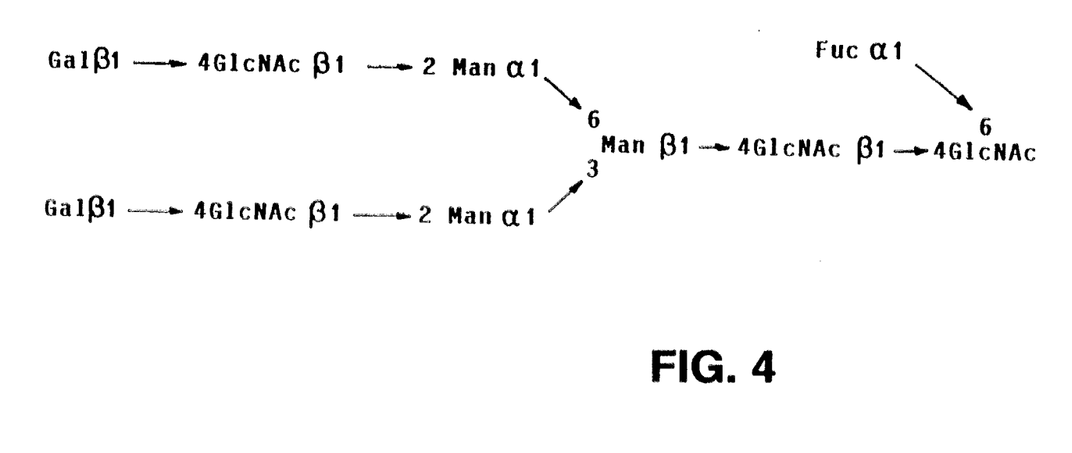
Figure 5:
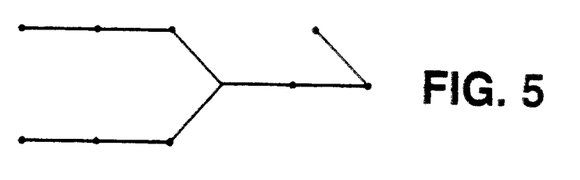
FIGS. 5–8 show four groups of structural possibilities with a given set of monosaccharides.

The sample used for analysis was NA2F, which has the composition shown in FIG. 4.

Monosaccharide composition analysis of the sample gave,

Mannose=3
Galactose=2
GlcNAc=4
Fucose=1

Four groups of structural possibilities can be derived from a composition having these monosaccharides in these proportions and these four structures are shown in outline respectively in FIGS. 5, 6, 7 and 8. In addition, the structures shown in these Figures give multiple variants in the following numbers, FIG. 5–9 variants
FIG. 6–18 variants
FIG. 7–12 variants
FIG. 8–6 variants Within each group, all variants of bond numbering are included and both core and outer arm fucosylation are accounted for. The above variants give a set of 45 candidates structures and this was confirmed by the computer expert system, which successively recommended the use of the following enzymes with the results shown,

| Enzyme to use | Monosaccharide detected | Candidate structures remaining |
|---|---|---|
| Jack bean alpha man (non arm-specific) | None | 27 |
| Bovine testis beta gal | Gal = 2 | 9 |
| Dip.P.beta hex | GlcNAc = 2 | 1 |

Figure 6:
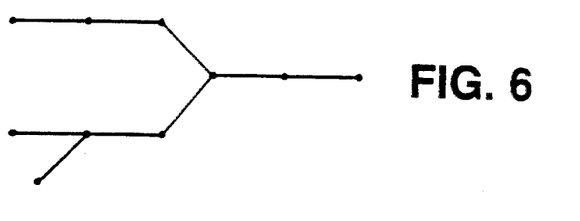
Figure 7:
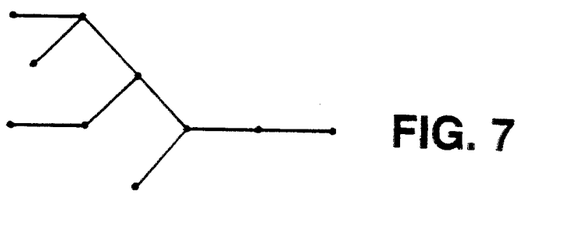
Figure 8:
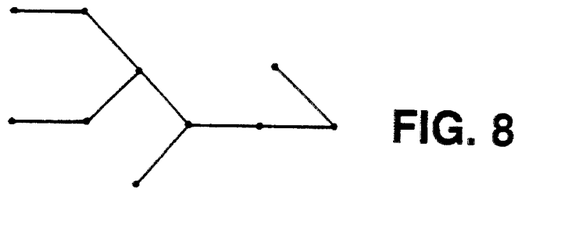

The variants of FIGS. 7 and 8 are eliminated by the first experiment, because these would yield mannose if treated with the alpha-mannosidase, whereas the putative test sample yielded none. The variants of FIG. 6 are eliminated by the second experiment, which yielded two galactose, whereas the presence of the outer arm fucose branch in FIG. 6 blocks the action of the galactosidase on that branch. Finally, of the nine remaining structures of FIG. 5, only the structure given would yield two N-Acetyl Glucosamine entities when reacted with the enzymes in the sequence given.

In this sequence, the structure is uniquely identified.

We claim:

1. Apparatus for sequencing an unknown oligosaccharide, comprising first means for deducing a set of oligosaccharide structures of which the unknown oligosaccharide is assumed to be a member, second means for simulating the effect of applying each one of a series of sequencing agents to each of said set of oligosaccharide structures and third means for determining the sequencing agent likely to give the most structural information if applied to the unknown oligosaccharide.

2. Apparatus as claimed in claim 1, in which the first means comprises means for determining a property of the unknown oligosaccharide which depends on its structure.

3. Apparatus as claimed in claim 2, in which the property is the number and type of each monosaccharide in the unknown oligosaccharide.

4. Apparatus as claimed in claim 2, in which the property is the retention time of said unknown oligosaccharide on a liquid chromatography column.

5. Apparatus as claimed in claim 1, in which the second means comprises means for consulting a set of rules which determine the effect of applying each of said sequencing agents to an oligosaccharide structure.

6. Apparatus as claimed in claim 5, in which the third means includes means for performing an exhaustive search among the predicted products of reaction of among the predicted products of reaction of all said set of oligosaccharide structures.

7. Apparatus as claimed in claim 6, in which the third means comprises means for calculating the distribution of the predicted products of reaction for all the structures in the set of oligosaccharide structures.

8. A method of sequencing an unknown oligosaccharide comprising deducing a set of oligosaccharide structures of which the unknown oligosaccharide is assumed to be a member, simulating the effect of applying each one of a series of sequencing agents to each of said set of oligosaccharide structures and determining the sequencing agent likely to give the most structural information if applied to the unknown oligosaccharide.

9. A method as claimed in claim 8, wherein deducing the set of oligosaccharide structures comprises identifying at least one basic structure from which a set of sub-structures can be generated by deleting monosaccharides from the at least one basic structure in all possible ways, and further identifying a set of candidate structures from among the set of sub-structures of which the unknown oligosaccharide is assumed to be a member.

10. A method as claimed in claim 8, including calculating the distribution of the predicted products of reaction for all the oligosaccharide structures in the set of oligosaccharide structures by consulting a set of rules which determine the effect of applying each of said sequencing agents to an oligosaccharide structure.

11. A method as claimed in claim 10, including conducting an experiment by contacting the unknown oligosaccharide with the agent or agents selected in accordance with the set of rules and comparing the actual experimental result with the calculation.

12. A method as claimed in claim 11, including eliminating structures from the candidate set which are inconsistent with the results obtained from an experiment and determining the next experiment based on the structures remaining.

13. A method as claimed in claim 12, in which the process is repeated until no further elimination is possible with the given sequencing agents.

* * * * *